United States Patent [19]
Piazza et al.

[11] Patent Number: 5,962,459
[45] Date of Patent: Oct. 5, 1999

[54] THERAPEUTIC ACTIVE AGENT FOR TREATMENT OF NEURON DEGENERATIVE DISEASES

[75] Inventors: Cinzia Piazza; Vincenzo Politi, both of Rome; Mario Materazzi, deceased, late of Rome, all of Italy, by Marcella Presenti Materazzi, Vanna Carla Materazzi, heiresses

[73] Assignee: Polifarma S.p.A., Rome, Italy

[21] Appl. No.: 08/862,306

[22] Filed: May 23, 1997

Related U.S. Application Data

[60] Provisional application No. 60/018,543, May 29, 1996.
[51] Int. Cl.$^6$ .................................................. A61K 31/55
[52] U.S. Cl. ............................................................. 514/269
[58] Field of Search ............................................. 514/269

[56] References Cited

FOREIGN PATENT DOCUMENTS

| 0178267 | 4/1986 | European Pat. Off. . |
| 0348360 | 12/1989 | European Pat. Off. . |
| 0462075 | 12/1991 | European Pat. Off. . |

OTHER PUBLICATIONS

W.K. Engal, "Uridine as a Possible Treatment for Amyotrophic Lateral Sclerosis (ALS): Hypothesis and Phase–I Study Demonstrating Safety", Neurology, vol. 38, No. 3, supplement 1, p. 326, Mar., 1988.

S.A. Keilbaugh et al., "Anti–Human Immunodeficiency Virus Type 1 Therapy and Peripheral Neuropathy: Prevention of 2',3'–Dideoxycytidine Toxicity in PC12 Cells, a Neuronal Model, by Uridine and Pyruvate", Molec. Pharmacology, vol. 44, No. 4, pp. 702–706, Oct., 1993.

G. Benzi et al., "Recovery After Hypoglycemic Brain Injury", Biochemical Pharmacology, vol. 32, No. 6, pp. 1083–1091, Mar. 15, 1983.

T.D. Wakade et al., "Adenosine–Induced Apoptosis in Chick Embryonic Sympathetic Neurons: A New Physiological Role for Adenosine", Journal of Physiology, vol. 488, No. 1, pp. 123–138, Oct., 1995.

Merck & Co., "The Merck Index", Twelfth Edition, pp. 1113–1114, 1996.

Patent Abstracts of Japan, JP 05 304951, vol. 18, No. 111, Nov. 19, 1993.

Chemical Abstracts AN 1986:418201, Agnati et al, "Intravenous uridine treatment antagonizes hypoglycemia–induced reduction in brain somatostatin–like immunoreactivity", Acta Physiol. Scand., 126(4), 525–31, Jan. 1986.

Chemical Abstracts AN 1992:242332, Mervis et al, "Exongenous nerve growth factor reverses age–related structural changes in neocortical neurons in the ageing rat", Ann. N.Y. Acad. Sci., 95–101, Jan. 1991.

*Primary Examiner*—Keith D. MacMillan
*Attorney, Agent, or Firm*—Browdy and Neimark

[57] ABSTRACT

Uridine is a therapeutic agent active as a growth promoter for treatment of neuron degenerative diseases deriving from pathological ageing or selective destruction, in particular Uridine shows the same biological effects as NGF, when added at low doses to the culture medium, so that uridine may replace NGF as therapeutic agent in neural diseases and it may be also associated with other growth factors that allow differentiation of neurons, or with anti-cancer and anti-virus drugs that cause neuron damage. In addition uridine shows important trophic properties on various types of cultured cells, stimulating cell reproduction when used at rather high dose levels.

31 Claims, No Drawings

THERAPEUTIC ACTIVE AGENT FOR TREATMENT OF NEURON DEGENERATIVE DISEASES

This application claims benefit of Provisional Appl. 60/018,543, filed May 29, 1996.

BACKGROUND OF THE INVENTION

1. Field of the Invention

The present invention relates to a new therapeutic use of uridine in neuron degenerative diseases resulting from pathological ageing or from functional losses due to various causes, for example peripheral neuropathies, lateral amyotrophic sclerosis and Alzheimer's disease. This invention follows the evidence of the effects of uridine administering on various types of cells cultured.

According to the present invention in fact, uridine can act as a growth promoter when added to cell cultures, producing different effects due to the dose-levels (high or rather low) and the type of cells used as a target, and in particular when administered to neuronal and glial cell lines, uridine has the same biological effects as Nerve Growth Factor.

2. Description of the Prior Art

Growth factors constitute a large family of proteins fundamentally devoted to reproduction, differentiation, maturation and survival of cells. In the last few years, the tremendous developments in protein production through genetic engineering and biological techniques led to important discoveries on the physio-pathologic roles in mammalian bodies of several growth factors: as hyper- or hypo-production of growth factors by nearby or circulating cells has been linked to a large number of unrelated diseases, such as diabetes, angiogenesis, stroke, hypertensive arterial hypertrophy, atherosclerosis, restenosis, glomerular nephritis, cancer and so on.

As regards specifically cells of the Central Nervous System (CNS), since late 1950's it has been shown that the mammalian neuronal development is controlled by a family of growth factors, later called neurotrophins, whose most important member appears to be Nerve Growth Factor (NGF). NGF was purified in the early 1970's, and subsequently has been cloned and sequenced. The native peptide consists of three pairs of subunits, of which the active one is a 118 residue beta-subunit. It is now well established that NGF exerts its effects on defined cell populations of neurons within the CNS, where specific receptors have been identified, cloned and sequenced: its mechanism of activity appears related to increased expression of early response genes inside the cells, leading to changes in the genetic program.

The effects of administration of uridine in brain have also been observed, and it has been shown uridine is able to protect against experimental epilexy and other neural pathology. The Applicant, for example, has already obtained a U.S. Pat. No. 4,960,759 for the use of uridine as a drug modulating the effects of dopamine in the Central Nervous System and, more recently, another U.S. Pat. No. 5,190,948 for treatment of the complications of diabetes at the peripheral nervous system level. The effects of administration of uridine however are not limited to Nervous System.

In general, in fact, uridine is a known compound that has been widely studied ever since it was found to be a constituent element of ribonucleic acids. The large variety of pharmacological effects of uridine lies in the fact that this pyrimidinic nucleoside, as well as forming part of the ribonucleic acids, and thus stimulating biosynthesis of proteins inside the cells, also superintends a number of fundamental biochemical processes, such as the reconstitution of glycogen reserves from glucose, detoxification of cells from numerous exogenous components, and biosynthesis of important constituents that are of structural importance for the cell functions, such as glycolipids and glycoproteins.

The effects of administration of uridine, either alone or associated with cytidine (another pyrimidinic nucleoside), have been studied in various organs in experimental animals: for example, it has been seen in a number of studies that on the isolated heart uridine has positive effects on the use of energy reserves, and improves the myocardial functions. At a muscular level, uridine increases glucose pick-up and biosynthesis of glycogen deposits. In the liver it improves hepatic regeneration after experimental intoxication.

Uridine is also one of the most important agents for the recovery of cell functions in mammals, and for this reason its concentration in the plasma is kept at more or less constant levels by means of enzymatic mechanisms, located above all in the liver. When the blood levels are too low (for example, as a result of damage to the liver) the uridine can be formed ex novo using a complex enzymatic system, comprising a transfer of electrons inside the mitochondrions: however, if the mitochondrions are not functioning adequately, as is the case during ageing or as a result of cell intoxication, then the external supply of uridine through the blood stream becomes of fundamental importance, lack of supply resulting in degeneration and subsequent death of the cells involved. Moreover external uridine is quickly and easily taken up through the outside membrane of the cell.

The ability of exogenous uridine to be used rapidly for biosynthesis of cell ribonucleic acids has been used therapeutically for a long time. There are a number of anti-tumour drugs available whose molecular structure is based on that of uridine, so that cells in rapid growth pick them up in large quantities, thus becoming intoxicated by altered chemical functions, which do not allow correct protein biosynthesis. In particular it has been demonstrated experimentally that anti-viral and anti-tumour agents cause important damage at a mitochondrial level (see, for example, Biochemical Pharmacology 38, 1033–1036, 1989, id. 42, 1397–1400, 1992), and are responsible for even fatal side effects, which can be observed in their long-term use (see, for example New England J. Med. 322, 1098–1105, 1990; id. 333, 1146–1148, 1995).

Unfortunately this biological damage is not only caused to the malign cells, but also spreads to healthy cells when these need to produce new proteins, so that use of the above mentioned drugs is strongly limited by their systemic toxicity. To overcome this problem, in order to allow the healthy cells to return to normal activity after intoxication by the anti-tumour agents, in recent years a special therapy has been perfected, which foresees the use of large amounts of uridine immediately after the use of anti-tumour agents such as 5-fluorouracyl, which is considered to be the reference drug for cancer of the colon (see for example Seminars in oncology 19, supp.3, 148–154, 1992).

Likewise important anti-viral agents, such as those currently in use to treat patients suffering from AIDS, are based on structures similar to uridine, in order to "intoxicate" the biosynthesis of viral proteins, or to inhibit the activity of particular enzymes (for example reverse transcriptase). In this case also, however, healthy cells are adversely affected, which theoretically might be prevented by administration of uridine: it has in fact been demonstrated "in vitro" on cell cultures that uridine is capable of abolishing the toxicity of azidodeoxythymidine (AZT) in human cells producing bone marrow (antimicrobial Agents and Chemotherapy 32, 997–1001, 1988) and, alongside pyruvate, that of Dideoxycytidine in PC12 cells (Molecular Pharmacology 44, 702–706, 1993). In spite of these results no drug composition based on uridine is actually in trade.

The reasoning behind the use of uridine, both in the case of the anti-tumour drug 5-fluorouracyl, and in case of the anti-viral drugs AZT and dideoxycytidine, is that there is competition on the part of the cells to pick up the pyrimidinic nucleosides, and even if it is not possible to reach an ideal situation in which the harmful cells pick up the pharmaceutical agents, while the healthy ones use the uridine, however it can be supposed that, by administering high doses of uridine after the drugs, the healthy cells can return to a normal level of activity, "pushing out" by competition the drugs from the sites they occupy in the ribonucleic acids.

SUMMARY OF THE INVENTION

According to the present invention uridine is capable of acting as a growth promoter stimulating various cell types to proliferate and differentiate in a sustained and extensive manner. In particular uridine shows biological effects quite similar to Nerve Growth Factor's, when administered to neuronal or glial cell lines.

It has now been found, and this forms the basis of the present invention, that uridine is capable not only of reverting the harmful effects induced in cell cultures by important anti-tumour and anti-viral drugs, but, and this is by far more important, that it can act as a growth promoter. In fact it can stimulate various types of cells to proliferate in a sustained and extensive manner, when administered at fairly high doses. On tumour cell lines of CNS, it can also promote cell differentiation and maturation when administered chronically at rather low doses, showing the same biological effects of NGF. In particular in fact we discovered that uridine can give the same results of the NGF when the growth factor is withdrawn from the medium.

This opens the road to a new therapeutic use of uridine, alone or associated with neurotrophins, in important degenerative situations of Nervous System, for which at the present time no adequate forms of treatment exist, due both to pathological ageing and to loss of function for other causes. As examples of the above mentioned diseases it is possible to mention non-diabetic peripheral neuropathies, lateral amyotrophic sclerosis and Alzheimer's disease.

This follows the finding that the deficiency of NGF and several other neurotrophins is probably involved in neurodegenerative diseases due to ageing of the brain or selective destruction of cell population. Hence both NGF and other neurotrophins are at present under study in models of many important diseases of the CNS (e.g. Alzheimer's disease, Stroke, Amyotrophic Lateral Sclerosis, Parkinson's disease), and pharmacological and clinical studies underway have been recently reported in a book ("Growth Factors as drugs for neurological and sensory disorders", John Wiley and sons, 1996). In fact NGF is at present used extensively in clinical trials in patients with Alzheimer's disease, with diabete peripheral neuropathies, and with peripheral neuropathies due to antiviral (e.g. anti-AIDS) and antitumour therapies. Unfortunately, the proteic nature of these substances makes their systemic administration particularly difficult. Therefore uridine can be considered as an advantageous substitute for NGF and other growth factors, because is well known that it is absorbed by the oral route, maintains steady-state levels in blood, is absolutely safe, and crosses the BBB (J. Natl. Cancer Inst. 83, 437–41, 1991; J. Neurochem. 45, 1411–18, 1985).

Hence an object of the present invention is the therapeutic use of uridine alone or associated with proteins defined as neuron growth factors for treatment of diseases deriving from pathological ageing or from selective neuron degeneration in man.

A further object of the present invention is a pharmaceutical composition comprising uridine at rather low doses as a trophic agent, alone or with proteins defined as neuron growth factors, along with pharmaceutically compatible excipients, for the treatment of human diseases deriving from pathological ageing or from selective neuron degeneration.

An additional object of the present invention is the use of uridine in association with anti-tumour and anti-viral drugs to ameliorate the harmful effects on peripheral nervous system induced by the latter.

EXPERIMENTAL DESCRIPTION

To define the role of uridine on mammal cell cultures, first two tests were used, commonly in practice in cell biology laboratories: the cell growth study and the proliferation test. As we have seen the capability of uridine to act as a growth factor, we tested the effects of its administration on both neuronal and glial cell lines, to define a possible association with NGF or other neurotrophins.

CELL GROWTH STUDY

To study the effects of uridine on cell growth in the presence of the drug AZT, it was decided to use the cell line Friend (murine erythroleukaemia); these cells represent a good experimental model for in vitro reproduction of the toxicity of AZT on in vivo haemopoietic progenitors of bone marrow.

The cells were cultivated in DMEM medium (Dulbecco's Modified Eagle's Medium), with the addition of 10% of FCS (Fetal Calf Serum), 1000 U/ml of penicillin and 1000 U/ml of streptomycin, and grown in incubators at a temperature of 37° C., a $CO_2$ concentration of 7% and a humidity of 98%. The cells underwent routine control three times a week, and were kept at a standard growth concentration of $0.3 \times 10^6$ per ml of medium.

Subsequently, the cells were measured at a concentration of $0.5 \times 10^5$ per ml in the normal culture medium, with the addition of various concentrations of AZT in the presence and in the absence of various doses of uridine. The cultures were monitored in these conditions for two weeks. Every 48 hours the culture medium containing the drugs was renewed and simultaneously cell growth was checked by microscope count in Neoubauer chambers. Before counting, the cells were coloured with Trypan blue so as to exclude the cells in necrosis from the growth curve. The time required to double the number of cells was then calculated, basing it on the increase in the number of cells observed every two days.

The inhibitory effect of AZT on cell growth, in the presence or in the absence of uridine, was evaluated as a percentage inhibition on doubling of the number of cells, using a simple proportion: the number of cells per ml in the presence of AZT (with or without uridine) divided by the number of cells per ml in the control (treated with the culture medium alone), the whole multiplied by the factor 100. Each test was carried out in triplicate.

TABLE 1

Cell growth using AZT with addition of uridine (UR) (doses in micro M)

| Drug | AZT | UR | % growth |
|---|---|---|---|
| Control | 0 | 0 | 100 |
| AZT | 0.1 | 0 | 70 |
| AZT + UR | 0.1 | 0.1 | 80 |
| AZT + UR | 0.1 | 0.2 | 85 |
| AZT + UR | 0.1 | 0.5 | 88 |
| AZT | 1 | 0 | 53 |
| AZT + UR | 1 | 1 | 75 |
| AZT + UR | 1 | 2 | 80 |
| AZT + UR | 1 | 5 | 82 |
| AZT | 10 | 0 | 45 |
| AZT + UR | 10 | 10 | 78 |
| AZT + UR | 10 | 20 | 67 |
| AZT + UR | 10 | 50 | 70 |

Table 1 shows the results obtained by treating the cells with different doses of AZT and uridine. The AZT was used at doses of 0.1, 1 or 10 micro M. As regards uridine, this was used in concentrations equivalent to 1, 2 or 5 times that of AZT. As can easily be seen from table 1, AZT produces a dose-dependent reduction in cell growth, while uridine is capable of partially antagonising this effect, recovering most of the growth levels seen in the absence of the anti-viral drug.

It can also be noted that, with the exception of an anomalous value found when both AZT and uridine are added at a concentration of 10 micro M, the effect of uridine is always dose-dependent.

However, the absence of total reversion of the toxic effects caused by AZT, together with the fact that the recovery of cell growth, in percentage compared with the cells that are not damaged by the anti-viral drug, increases in proportion to the amount of uridine used, makes it possible to think that the phenomenon is not due to protection from the toxic agent (AZT), but to a stimulation of the proliferation induced by uridine on the cells that remain intact. To verify this hypothesis, two different cell proliferation tests were therefore carried out.

CELL PROLIFERATION TEST 1

This first test was carried out on two types of cell line, to evaluate the effect of high doses of uridine on proliferation, in the presence of AZT or of dideoxycytidine, the two anti-viral drugs currently in use for treatment of patients suffering from AIDS. The cells used were Friend (murine erythroleukaemia) and CEM (human lymphoblast leukaemia). The cells were planted in 96-well plates at a concentration of 5000 cells in 200 microliters of medium per well (approximately 25000 cells per ml). The cultures were left to incubate for 48 hours, after which each well was market with 1 microCurie of timidine tritiate and, after 18 hours, harvested onto fibre filters, so that each filter disk corresponded to one well. Cell proliferation was evaluated in terms of timidine tritiate incorporation into the cell culture: the use of a bent-counter allowed the amounts of beta radiation released by each disk to be measured, as a number of counts per minute (cpm). The values given are an average of the cpm of cultures performed in triplicate.

TABLE 2

Proliferation of Friend cells under the effects of AZT with and without the addition of uridine (UR) (doses indicated in microM)

| | UR dose | Proliferation response in cpm | | | |
|---|---|---|---|---|---|
| AZT Dose | 0 | 50 | 100 | 200 | 300 |
| 10 | 4000 | 32000 | 41000 | 68000 | 70000 |
| 25 | 3000 | 17000 | 65000 | 76000 | 77000 |
| 50 | 2000 | 11000 | 11000 | 28000 | 35000 |

The response of the medium in the absence of additions is 12000 cpm.

TABLE 3

Proliferation of CEM cells under the effects of ddC, with and without the addition of uridine (UR) (doses indicated in microM)

| | UR dose | Proliferation response in cpm | | | |
|---|---|---|---|---|---|
| ddC Dose | 0 | 50 | 100 | 200 | 300 |
| 10 | 3000 | 5000 | 20000 | 22000 | 38000 |
| 25 | 2000 | 3000 | 12000 | 21000 | 30000 |
| 50 | 1000 | 2000 | 13000 | 13000 | 21000 |

The response of the medium in the absence of additions is 5000 cpm.

As can easily be seen from tables 2 and 3, uridine has clear stimulation effects on cell proliferation, which go well beyond recovery of the inhibitory action due to anti-viral drugs. As regards the Friend cells, the effect of AZT is already completely reverted when the uridine is added at a dose of 50 microM, while at higher concentrations (100, 200, and 300 microM) a powerful dose-dependent stimulation of cell proliferation can be seen, reaching levels 6 or 7 times higher than the base level (that is to say the level observable in the absence of drugs). In CEM cells, the effect is qualitatively the same, although a complete reversion of the inhibitory effect due to dideoxycytidine can only be seen starting from a uridine dose equivalent to 100 microM.

It is therefore possible to conclude that, at high doses, uridine has the effect of stimulating proliferation in both cell lines that goes well beyond recovery of the activity lost through administration of anti-viral drugs.

CELL PROLIFERATION TEST 2

Using the method described above, the effect of uridine was tested on four different types of mammalian cell (two mouse and two human), to observe whether or not the potential cell proliferation stimulation effect is also evident in the absence of anti-viral drugs. The cells used were the two described above (Friend and CEM), plus the Jurkat (human T-lymphocyte leukaemia) and C2C12 (from the rat skeleton musculature).

TABLE 4

Effect of uridine on cell proliferation
% increase in growth in different human and murine cell types

|        | Uridine 50 μm | Uridine 100 μm | Uridine 200 μm | Uridine 300 μm |
|--------|---------------|----------------|----------------|----------------|
| FRIEND | +87%          | +770%          | +1000%         | +1033%         |
| JURKAT | +27%          | +49.3%         | +495%          | +1400%         |
| CEM    | +14%          | +198%          | +368%          | +1098%         |
| C2C12  | +219%         | +235%          | +374%          | +405%          |

As can be seen from table 4, uridine is capable of stimulating in a dose-dependent manner the proliferation of all the cell lines tested, even in the absence of anti-viral drugs. Moreover there is a difference in the extent of proliferation stimulation from one cell type to another (for further consideration see results below). These findings show that uridine can act as a growth promoter when administered at rather high concentration on various types of cell culture, suggesting an active role in the mechanism of cellular growing and development.

EFFECTS OF URIDINE ON GROWTH AND DIFFERENTIATION OF HUMAN TUMOUR CELL LINES OF NEURONAL AND GLIAL ORIGIN

As the capability of uridine to act as a growth promoter was proven, a carefully designed experiment has been performed, with the aim to test effects of uridine, with or without beta-NGF (Nerve Growth Factor, which is the best studied growth promoter of cells located in the CNS), on the growth and differentiation of tumour cell lines of central origin. That's because an uncontrolled growth of neuronal and/or glial cells is a devastating event for the CNS, leading to loss of functions and development of tumour masses. Therefore we wanted to check first the capability of uridine to act as a growth factor on the cells of CNS, secondly the likeness and differences with the action of the most important growth promoter of the neural and glial cells.

Two human cell lines have been used: CHP126 (a lowly differentiated cell line with a rounded cell body, only weakly positive to markers for neurofilaments 200 Kda, derived from a neuroblastoma of the sympatethic nervous system) and T67 (a cell line selected from glial tumour, defined as an astrocytoma of III degree according to WHO classification, and cultured at Rome University lab of Prof. G. M. Lauro). Cells were cultured in the DMEM Dulbecco medium, with addition of 5% fetal bovine serum, 1% glutamine, 1% Hepes and 1% gentamycin. Cells were maintained in incubator at 37° C. and humidified atmosphere with 5% $CO_2$.

Cells were put on plates with wells (roughly 20,000 cells per well) and treated the day after with uridine and/or beta-NGF: uridine was used at two dose levels (1 and 10 micrograms per milliliter, equivalent to a dose level in vivo of 300–2000 mg/day in humans), while beta-NGF was administered at 100 nanograms per milliliter.

Cell proliferation was evaluated calculating cell numbers in wells (with a microscope) and using the MTT method: after addition of MTT (3-(4,5-dimethylthiazole-2yl) 2,5-diphenyl bromide) and a lysing buffer, colour development was followed with a spectrophotometer (560 nm). In order to avoid interferences due to the dead cells, cells were counted at the microscope after addition of the Trypan blue.

Differentiation was evaluated using immunofluorescent methods against neurofilaments 200 Kda (for neuronal cells) or against the acidic gliofibrillar protein (for glial cells) after antibody reactions, samples were observed at a microscope under fluorescence.

RESULTS

As can be seen from the experiment of cell growth study and proliferation test, uridine is capable of stimulating in a dose-dependent manner the proliferation of all the non-neuronal cell lines tested, even in the absence of anti-viral drugs. Although there is a difference in the extent of proliferation stimulation from one cell type to another, it can be stated that the effect usually starts to be seen at a dose of 50 microM of uridine, and becomes extraordinarily effective at a dose of from 100 microM up. It is also interesting to note that, in the cell line C2C12, (see table 4) the effect is already very strong at the lowest concentration (219% increase at 50 microM). This might mean that stimulation of cell proliferation by uridine on certain types of cell already occurs at doses in use in pharmacology (plasmatic levels of this size are obtained in humans by administration of approximately 1–2 grams of uridine).

According to the elements obtained from the experiments, performed on the cell lines CHP126 (neural) and T67 (glial), with or without the NGF, both uridine and beta-NGF, when used alone, were unable to modify proliferation of the tumour cell lines measured after three days. On the other hand, when NGF was added with uridine (at both concentration), the proliferation of cells after three days appeared reduced to roughly 45% of untreated samples.

With respect to differentiation, observations at the microscope under fluorescence showed clear long-term (1 to 3 weeks) effects of uridine and/or beta-NGF on the markers of well-matured cells (neurofilaments in neurons and gliofibrillar protein in glial cells): in fact, both uridine and beta-NGF induced an elongation of neurofilaments and increased production of gliofibrillar protein.

These processes were reverted by suspension of both treatments. Moreover when uridine (both doses) was administered chronically together with beta-NGF, a better expression of the markers was observed (synergistic effect between uridine and beta-NGF) and the use of uridine at low doses (1 microgram/milliliter) was able to recover beta-NGF effects when this protein was withdrawn from the medium after 1 week.

Overall the results of these latter experiments indicate that both uridine and beta-NGF stimulate differentiation, maturation and function of cell lines derived from human tumours growing in the CNS. Furthermore the chronic use of low levels of uridine can improve the effects obtained with beta-NGF and might substitute the pharmacological effects of the trophic factor on cells of the CNS.

FINAL CONCLUSIONS

The experiments illustrated above demonstrate for the first time that uridine, together with its well known properties of antagonist to the toxic effects of anti-tumour and anti-viral drugs at a mitochondrial level, has also a clear ability to stimulate the proliferation of both human and murine cells, when added at high concentrations to the cultivation media. The reason of this effect, only a small portion of which might be due to an increase in energetic substrates (for example the ribose) contained in the nucleoside molecule, is probably linked to the stimulated biosynthesis of trophic factors which regulate communications between cells in culture. When added at much lower levels to cultured tumour cell lines originating from the CNS, chronic uridine was able to stimulate differentiation and functioning, so mimicking the effects of beta-NGF. As a consequence, uridine can be used in a number of pathological situations in which specific nerve cell populations have been damaged, and is necessary to reconstruct the integrity of the tissues by stimulating proliferation and differentiation of the remaining healthy cells.

A first set of clinical indications in which uridine can be used in order to exploit its pharmacological characteristics showed in the present experiments, are the pathological consequences on peripheral nerves (peripheral neuropathies) especially when induced by antiviral, antitumour or immunosuppressant drugs acting with antagonism on uridine biosynthesis or utilisation by cells. It is also important to note that, in spite of well known "uridine rescue therapy" presently suggested for people undergoing antitumour treatments (in which doses of dozen of grams are used every few hours over a period of two or three days), a more rational approach deduced from the present assays is to administer chronically a much lower amount of uridine for a better recovery of healthy cells and differentiation of the tumoral ones.

Another and most important group of indications linked to the newly demonstrated properties of uridine as a growth promoter capable of mimicking NGF's action, are those coming from pathological losses of neurons inside the CNS, e.g. Alzheimer's disease, Parkinson's disease, Stroke and any event producing destruction of functional neurons.

In recent years in fact a number of trophic factors produced by nerve cells have been identified and tested for the treatment of important degenerative diseases leading to loss of function. Thus, alongside the Nerve growth factor (NGF), discovered a few decades ago, today we also speak of the Brain-derived growth factor (BDGF), neurotrophin-3 (NT-3), Neurotrophin 4/5 (NT-4/5), ciliary neurotrophic factor (CNTF) fibroblast growth factor (FGF), insulin-like growth factor (IGF-I), transforming growth factor beta (TGF beta) and glial-derived growth factor (GDGF), to name but a few.

Many of these factors are currently being studied, and some have reached the level of clinical studies, for the treatment of diseases, such as neuropathies produced by anti-tumour or anti-viral drugs, lateral amyotrophic sclerosis or Alzheimer's disease. In particular examples include beta NGF tested in diabetic neuropathies, taxol neuropathy, compressive neuropathy, AIDS related neuropathy, Alzheimer's disease; and CNTF studied in amyotrophic lateral sclerosis; NT-3 assayed in large fiber neuropathy; and IGF-I tested in amyotrophic lateral sclerosis, vincristine neuropathy and taxol neuropathy. Many other factors are discovered, even if their potential therapy is not yet established (e.g. GDGF, FGF and so on; see for example TINS 18, 463–464, 1995).

Unfortunately, the proteinaceous nature of these substances makes their systemic administration particularly difficult and renders it practically impossible to reach the CNS. That constitutes the major problem of the clinical use of these factors.

The discovery that uridine (that can be administered by the oral route and reaches easily the CNS from blood circulation), added to neural or glial cell cultures at low concentrations (that can be reached in the plasma by oral administration of pharmacological doses), has the same powerful effects of NGF, makes it possible to propose this compound as a good alternative to NGF and the other said trophic factors, and suggests its administration alone or in association with recognised neurotrophic agents, for the treatment of invalidating diseases deriving either from pathological ageing, or from the degeneration of specific cell populations. Examples of this type of disease are the peripheral neuropathies caused by drugs, lateral amyotrophic sclerosis and Alzheimer's disease.

Concerning the pharmaceutical doses which can be used in therapy, the value of 300–2000 mg/day is justified from the results obtained on cell culture, as a consequence of the following considerations.

In the culture medium the concentration of 4 micro M can be reached by administering uridine at dose levels of 1 mcg/ml, and in healthy people blood-levels of uridine are between 3 and 5 micro M. This physiological level of uridine can be increased up to a value of 12 micro M or also 25 micro M, administering single oral doses of uridine respectively of 500 mg and 1800 mg, with a return to basal levels after 5 hours (J. Natl. Cancer Inst. 83, 437–41, 1991). However the uridine concentration in the tissues is approximately ten times higher than the plasmatic one, owing to a mechanism of accumulation of the substance at the inner of the cells (Cancer Res. 46, 3490–4, 1986). These results imply that also dose-levels lower than 500 mg can give uridine concentration therapeuthically effective, when the level of substance in blood is not sufficient.

It is claimed:

1. A method for the treatment of disturbances of the nervous system due to degeneration of neuronal or glial cells in mammals, comprising administering to said mammals an effective amount of uridine to counteract said degeneration by stimulating cell growth.

2. A method according to claim 1 wherein said uridine is administered orally to humans at a dosage of 300 to 2000 mg/day for an extended period of treatment.

3. A method according to claim 1, wherein said disturbance of the nervous system is a peripheral neuropathy of iatrogenic origin.

4. A method according to claim 1, wherein said disturbance of the nervous system is Alzheimer's disease.

5. A method according to claim 1, wherein said disturbance of the nervous system is Parkinson's disease.

6. A method according to claim 1, wherein said disturbance of the nervous system is caused by a stroke.

7. A method according to claim 1, wherein said disturbance of the nervous system is lateral amyotrophic sclerosis.

8. A method for counteracting selective degeneration in neuronal or glial cells of a mammal, wherein said degeneration produces a disturbance in the nervous system of said mammal, comprising administering to said mammal an effective amount of uridine to promote differentiation and functioning and maturation of said cells.

9. A method according to claims 8 wherein said uridine is administered orally to humans at a dosage of 300 to 2000 mg/day for an extended period of treatment.

10. A method according to claim 8, wherein said disturbance of the nervous system is a peripheral neuropathy of iatrogenic origin.

11. A method according to claim 10 for reversing the harmful effects induced in the peripheral nervous system of a mammal by an administration to said mammal of an anti-viral drug for the treatment of a viral disease.

12. A method according to claim 11, wherein said viral disease is AIDS.

13. A method according to claim 10 for reversing the harmful effects induced in the cells of a mammal by an administration to said mammal of an anti-tumoural drug for the treatment of a tumoral disease.

14. A method according to claim 8, wherein said disturbance of the nervous system is Alzheimer's disease.

15. A method according to claim 8, wherein said disturbance of the nervous system is Parkinson's disease.

16. A method according to claim 8, wherein said disturbance of the nervous system is caused by a stroke.

17. A method according to claim 8, wherein said disturbance of the nervous system is lateral amyotrophic sclerosis.

18. In a method for promoting an action counteracting a selective degeneration of neuronal or glial cells of a mammal, said degeneration being associated with disturbances in the nervous system of said mammal which can be treated by administering to said mammal a therapeutically effective amount of neurotrophins, the improvement comprising administering to said mammal an effective amount of uridine in place of said neurotrophins to stimulate cell growth and promote differentiation and functioning and maturation of said cells.

19. A method according to claim 18, wherein said uridine is administered orally to humans at a dosage of 300 to 2000 mg/day for an extended period of treatment.

20. A method according to claim 18, wehrein said neuron growth factor is selected from the group consisting of NGF, BDNF, NT-3, NT-4/5, CNTF, FGF, IGF-I, TGF beta, and GTNF.

21. Method according to claim 18, wherein said uridine is administered with neurotrophins.

22. The method according to claim 21, wherein said neurotrophin is NGF.

23. A method according to claim 18, wherein said disturbance of the nervous system is a peripheral neuropathy of iatrogenic origin.

24. A method according to claim 18, wherein said disturbance of the nervous system is Alzheimer's disease.

25. A method according to claim 18, wherein said disturbance of the nervous system is Parkinson's disease.

26. A method according to claim 18, wherein said disturbance of the nervous system is caused by a stroke.

27. A method according to claim 18, wherein said disturbance of the nervous system is lateral amyotrophic sclerosis.

28. A composition for treating disturbances of the nervous system due to selective degeneration of neuronal or glial cells in mammals by stimulating cell growth and promoting differentiation and functioning and maturation of said cells comprising a pharmaceutically effective amount of uridine and at least one neurotrophin, wherein the proportion of uridine or neurotrophin is from 1:10 to 1:100 and pharmaceutically acceptable carriers and diluents.

29. A composition according to claim 18 for counteracting selective degeneration of neuronal or glial cells of a mammal, said degeneration being associated with disturbances in the nervous system of said mammal, said disturbances being capable of treatment by administration to said mammal of a therapeutically effective amount of neurotrophins.

30. The composition according to claim 18, wherein the neurotrophin is nerve growth factor.

31. A comosition according to claim 28, in which said disturbances are selected from the group consisting of Alzheimer's disease, Parkinson's disease, stroke, lateral amyotrophic sclerosis and peripheral neuropathy of iatrogenic origin.

* * * * *